(12) United States Patent
Heimbrock et al.

(10) Patent No.: US 7,637,464 B2
(45) Date of Patent: Dec. 29, 2009

(54) PATIENT SUPPORT WITH MOBILE IV STAND TRANSPORT HANDLE

(75) Inventors: Richard Henry Heimbrock, Cincinnati, OH (US); Stephen R. Hamberg, Cincinnati, OH (US)

(73) Assignee: Hill-Rom Services, Inc., Wilmington, DE (US)

( * ) Notice: Subject to any disclaimer, the term of this patent is extended or adjusted under 35 U.S.C. 154(b) by 151 days.

(21) Appl. No.: 11/622,077

(22) Filed: Jan. 11, 2007

(65) Prior Publication Data

US 2007/0176063 A1 Aug. 2, 2007

Related U.S. Application Data

(60) Provisional application No. 60/760,343, filed on Jan. 19, 2006, provisional application No. 60/804,227, filed on Jun. 8, 2006.

(51) Int. Cl.
*A47B 96/06* (2006.01)
*A47G 29/00* (2006.01)

(52) U.S. Cl. .............................. 248/218.4; 248/224.51

(58) Field of Classification Search ................ 180/65.1; 248/218.4, 224.51, 223.41, 231.71
See application file for complete search history.

(56) References Cited

U.S. PATENT DOCUMENTS

| | | | |
|---|---|---|---|
| 2,696,963 A | 12/1954 | Shepherd | |
| 3,709,372 A | 1/1973 | Alexander | |
| 3,709,556 A | 1/1973 | Allard et al. | |
| 3,872,945 A | 3/1975 | Hickman et al. | |
| 4,190,224 A | 2/1980 | LeBlanc et al. | |
| 4,225,104 A | 9/1980 | Larson | |
| 4,262,872 A | 4/1981 | Kodet | |
| 4,332,378 A | 6/1982 | Pryor | |
| 4,489,454 A | 12/1984 | Thompson | |
| 4,511,157 A | 4/1985 | Wilt, Jr. | |
| 4,511,158 A | 4/1985 | Varga et al. | |
| 4,600,209 A | 7/1986 | Kerr, Jr. | |
| 4,725,027 A | 2/1988 | Bekanich | |
| 4,767,131 A | 8/1988 | Springer et al. | |
| 4,795,122 A | 1/1989 | Petre | |
| 4,886,237 A | 12/1989 | Dennis | |
| 4,945,592 A | 8/1990 | Sims et al. | |
| 5,094,418 A | 3/1992 | McBarnes, Jr. et al. | |
| 5,117,521 A | 6/1992 | Foster et al. | |
| 5,135,191 A | 8/1992 | Schmuhl | |
| 5,149,036 A | 9/1992 | Sheehan | |
| 5,219,139 A | 6/1993 | Hertzler et al. | |
| 5,319,816 A | 6/1994 | Ruehl | |

(Continued)

FOREIGN PATENT DOCUMENTS

EP    1 810 652 A2    1/2007

(Continued)

OTHER PUBLICATIONS

European search report from EP 08 25 1082 dated Aug. 6, 2008.

*Primary Examiner*—Amy J. Sterling
(74) *Attorney, Agent, or Firm*—Barnes & Thornburg LLP (57) ABSTRACT

A patient support apparatus includes a frame, a plurality of casters coupled to the frame and supporting the frame above a floor, a push handle coupled to the frame, and an IV pole coupler coupled to the push handle.

27 Claims, 10 Drawing Sheets

U.S. PATENT DOCUMENTS

| | | | |
|---|---|---|---|
| 5,337,992 A | 8/1994 | Pryor et al. |
| 5,344,169 A | 9/1994 | Pryor et al. |
| 5,355,539 A | 10/1994 | Boettger |
| 5,366,191 A | 11/1994 | Bekanich |
| 5,407,163 A | 4/1995 | Kramer et al. |
| 5,421,548 A | 6/1995 | Bennett et al. |
| 5,499,721 A | 3/1996 | Hansen et al. |
| 5,527,289 A | 6/1996 | Foster et al. |
| 5,556,065 A | 9/1996 | Wadley |
| 5,647,491 A | 7/1997 | Foster et al. |
| 5,699,988 A | 12/1997 | Boettger et al. |
| 5,806,111 A | 9/1998 | Heimbrock et al. |
| 5,898,961 A | 5/1999 | Ambach et al. |
| 5,966,760 A | 10/1999 | Gallant et al. |
| 5,987,670 A | 11/1999 | Sims et al. |
| 6,073,285 A | 6/2000 | Ambach et al. |
| 6,079,678 A | 6/2000 | Schott et al. |
| 6,179,260 B1 | 1/2001 | Ohanian |
| 6,182,662 B1 | 2/2001 | McGhee |
| 6,296,261 B1 | 10/2001 | deGoma |
| 6,360,389 B1 | 3/2002 | Gallant et al. |
| 6,585,206 B2 | 7/2003 | Metz et al. |
| 6,704,956 B2 | 3/2004 | Riley et al. |
| 6,708,991 B1 | 3/2004 | Ortlieb |
| 6,725,483 B2 | 4/2004 | Gallant et al. |
| 6,966,086 B2 | 11/2005 | Metz et al. |
| 6,969,031 B2 | 11/2005 | Ugent et al. |
| 7,008,269 B2 | 3/2006 | Riley et al. |
| 7,065,812 B2 | 6/2006 | Newkirk et al. |
| 7,154,397 B2 | 12/2006 | Zerhusen et al. |
| 2002/0047075 A1 | 4/2002 | Metz et al. |
| 2003/0037375 A1 | 2/2003 | Riley et al. |
| 2005/0000019 A1 | 1/2005 | Newkirk et al. |
| 2006/0162077 A1* | 7/2006 | McDaniel et al. ............ 5/611 |
| 2006/0249641 A1* | 11/2006 | Bally et al. ............ 248/229.2 |

FOREIGN PATENT DOCUMENTS

| | | |
|---|---|---|
| WO | WO 97/49442 | 12/1997 |
| WO | 03/057126 A1 | 7/2003 |

* cited by examiner

PATIENT SUPPORT WITH MOBILE IV STAND TRANSPORT HANDLE

CROSS REFERENCE TO RELATED APPLICATIONS

This application claims the benefit of a U.S. Provisional Patent Application No. 60/760,343, filed Jan. 19, 2006, and entitled "Procedural Stretcher", and a U.S. Provisional Patent Application No. 60/804,227, filed Jun. 8, 2006, and entitled "Stretcher." The disclosures of the two U.S. Provisional Patent Application Nos. 60/760,343 and 60/804,227 are hereby incorporated by reference herein.

BACKGROUND OF THE INVENTION

The present disclosure generally relates to a patient support apparatus, such as a stretcher, having wheels or casters for transporting a patient. More particularly, the present disclosure relates to such patient support apparatus having push handles.

Transporting patients requiring the administration of medications intravenously using IV bags hung on floor supported, wheeled IV poles can be difficult. During transport, multiple caregivers may be needed for maneuvering the stretcher and an associated floor supported IV pole along the floor. It is known to provide stretchers with their own IV poles or with some type of mechanism for transporting a floor supported IV pole in tandem with the stretcher so that a caregiver does not have to hold the IV pole with one hand and push the stretcher with the other hand. It is also known to provide systems in which IV poles transfer from a wheeled cart to a stretcher or hospital bed. See U.S. Pat. Nos. 4,262,872; 4,945,592; 5,117,521; 5,319,816; 5,407,163; and 6,585,206 for examples of these various types of prior art devices.

Although the term "stretcher" is used throughout this disclosure, it is understood that the teachings of this disclosure may be incorporated into other types of patient support apparatuses, such as, for example, hospital beds, imaging tables, operating tables, and so on. The term "patient support apparatus," as used in this description and claims, therefore, shall be understood to include any type of patient support apparatus, such as, for example, a stretcher, a hospital bed, an imaging table, an operating table, and the like.

SUMMARY OF THE INVENTION

The present invention comprises an apparatus that has one or more of the features listed in the appended claims, or one or more of the following features or combinations thereof, which alone or in any combination may comprise patentable subject matter:

A patient support apparatus may include a frame, a plurality of casters coupled to the frame and supporting the frame above a floor, a push handle coupled to the frame, and an IV pole coupler coupled to the push handle. The IV pole coupler may comprise a hook or a flange that hooks around the IV pole. The push handle may have a generally upwardly extending first portion and a handle post that extends laterally inwardly relative to the first portion. The IV pole coupler may extend laterally outwardly relative to the generally upwardly extending first portion of the push handle. The IV pole coupler may be integrally formed with the handle post. The IV pole coupler and push handle may be configured so that a caregiver is able to grip the push handle and the IV pole simultaneously with one hand as the caregiver maneuvers the patient support apparatus and the IV pole along the floor. The IV pole may be retained in the IV pole coupler by the simultaneous grip of the caregiver's hand of the IV pole and the push handle.

In some embodiments, the IV pole coupler may have a first portion and a second portion that is movable relative to the first portion between a first position coupling the IV pole to the handle and a second position allowing the IV pole to be decoupled from the handle. In other embodiments, the IV pole coupler may comprise a flexible flap that is configured to deformingly wrap around the IV pole.

The apparatus may include a deck supported above the frame. The IV pole coupler may include a portion that extends outwardly past a side edge of the deck. The IV pole coupler may have a generally vertically-extending groove configured to receive the IV pole. The generally vertically-extending groove may open laterally inwardly toward a vertical plane passing through a longitudinal centerline of the frame. The IV pole coupler may have a flange portion configured to wrap around the IV pole when the IV pole is received in the vertically-extending groove. A top wall of the flange portion may taper downwardly toward a free end thereof.

The frame may include a lower frame supported by the casters and an upper frame supported by the lower frame. The push handle may be coupled to the upper frame. The push handle may be movable between a use position in which the IV pole coupler is located above the upper frame and a storage position in which the IV pole coupler is located below the upper frame.

Additional features, which alone or in combination with any other feature(s), such as those listed above and those listed in the appended claims, may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION OF THE DRAWINGS

Figure 1:
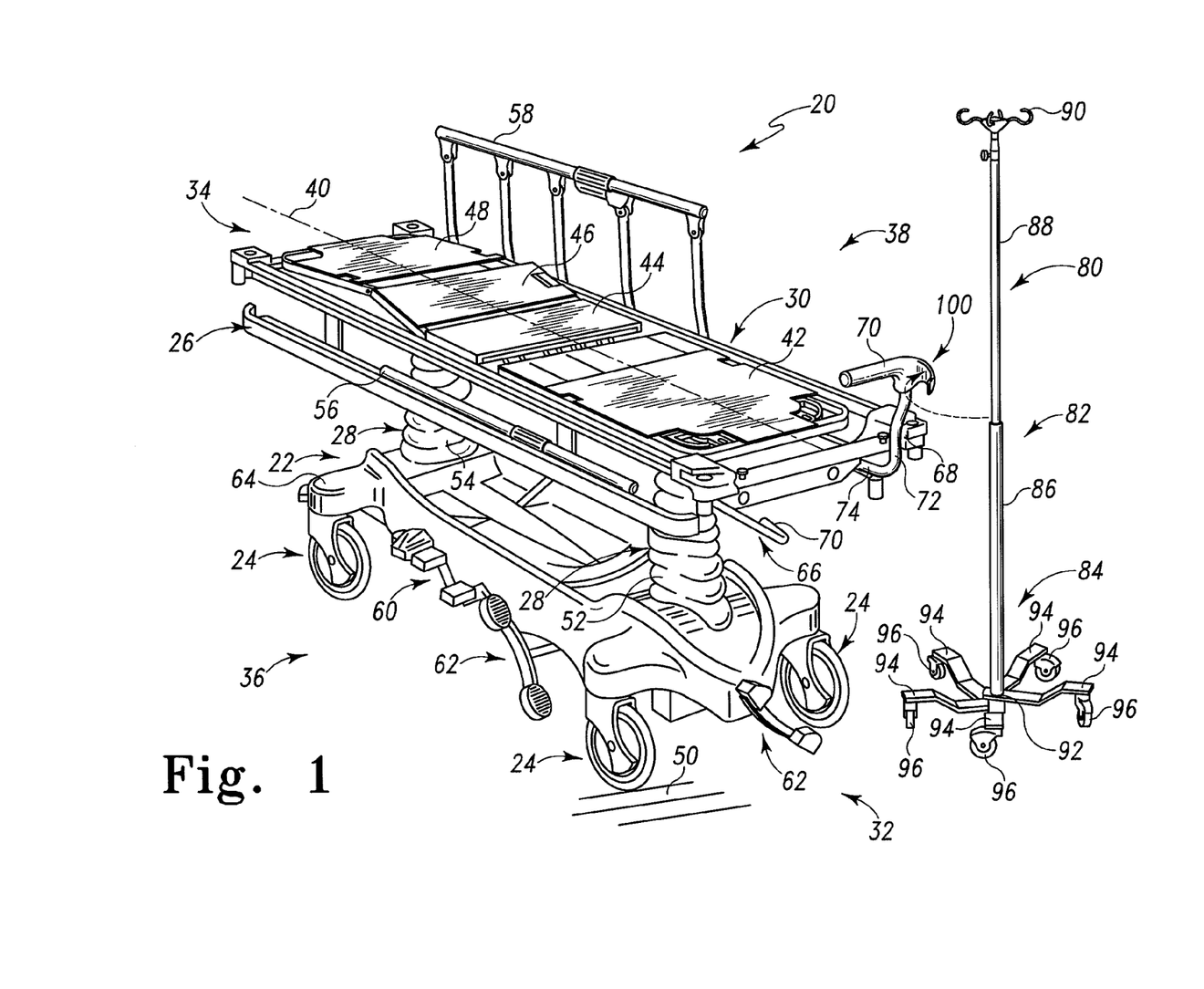
FIG. 1 is a perspective view of an illustrative stretcher and a mobile IV stand positioned next to the stretcher, showing the stretcher including a lower frame supported on casters, an upper frame supported by the lower frame, a deck carried by the upper frame, a pair of left and right push handles coupled to the upper frame near its head end with the left push handle in a lowered storage position and the right push handle in a raised use position, and an IV pole coupler coupled to a handle post of the right push handle, and showing the mobile IV stand including a wheeled base and an IV pole extending upwardly from the wheeled base.

FIG. 1 shows a patient support apparatus, such as a stretcher 20, and a mobile IV stand 80 positioned next to the stretcher 20. The stretcher 20 includes a lower frame 22 supported on casters 24, an upper frame 26 coupled to the lower frame 22 by an elevation adjustment mechanism 28, a patient support deck 30 carried by the upper frame 26, a head end 32, a foot end 34, an elongated left side 36, an elongated right side 38, and a longitudinal axis 40. The deck 30 includes laterally extending and longitudinally spaced head, seat, thigh and foot sections 42, 44, 46, 48. The deck sections 42, 44, 46, 48 define an upwardly-facing support surface that supports a mattress pad (not shown), which, in turn, supports a patient. A pair of collapsible side rails 56, 58 are mounted to the upper frame 26 adjacent to the left and right sides 36, 38 of the deck 30. Each side rail 56, 58 is independently movable between a lowered storage position (shown with respect to the left side rail 56) and a raised use position (shown with respect to the right side rail 58).

The elevation adjustment mechanism 28 is operable to raise, lower, and tilt the upper frame 26 relative to the lower frame 22. In the illustrated embodiment, the elevation adjustment mechanism 28 includes head and foot end hydraulic cylinders (not shown) covered by flexible boots 52, 54. Coupled to the lower frame 22 are a plurality of elevation adjustment pedals 60 and brake-steer pedals 62. The elevation adjustment pedals 60 are operable to raise and lower the upper frame 26, to control the vertical positions of the head and foot ends 32, 34 of the upper frame 26, and to tilt the upper frame 26. The brake-steer pedals 62 are operable to brake and unbrake the casters 24 and to raise and lower a steering wheel (not shown). A shroud 64 of the lower frame 22 covers the structure frame members (not shown) of the lower frame 22.

As shown in FIG. 1, a pair of push handles 66, 68 are mounted to the upper frame 26 near the head end 32 adjacent to left and right sides 36, 38 of the deck 30. Each push handle 66, 68 is independently movable between a lowered storage position (shown with respect to the left handle 66) and a raised push position (shown with respect to the right handle 68). When the push handles 66, 68 are locked in the raised push positions, a caregiver is able to grip the push handles 66, 68 to maneuver the stretcher 20 over a floor 50. In the lowered storage positions, the push handles 66, 68 are out of the way, thus maximizing a caregiver's access to a patient on the deck 30. The push handles 66, 68 each include a handle post 70 that is gripped by the caregiver when the caregiver moves the stretcher 20, a pivot post 74 pivotably coupled to upper frame 26, and a bent extension post 72 connecting the handle post 70 to the pivot post 74. The terms "grip," "grasp," and the like, are used interchangeably herein and each is intended to have the broad meanings of the other. The respective handle post 70, extension post 72, and pivot post 74 of each push handle 66, 68 are connected in a serpentine-like configuration. In the embodiment shown in FIGS. 1-4, when the push handles 66, 68 are in their respective raised push positions, the handle posts 70 extend generally perpendicularly to the longitudinal axis 40 of the frame 26. U.S. Pat. No. 5,806,111 discloses illustrative push handles that are movable relative to an upper frame of a stretcher between a lowered storage position and a raised push position. U.S. Pat. No. 5,806,111 is hereby incorporated by reference herein.

As shown in FIG. 1, a mobile IV stand 80 includes a vertically-extending column 82 supported on a wheeled base 84. In the illustrated embodiment, the column 82 includes a tube 86 secured to the base 84 and an IV pole 88 attached to the tube 86. In some embodiments, the IV pole 88 may telescope relative to the tube 86. In such embodiments, a manually operable locking mechanism (not shown) may be provided to releasably secure the IV pole 88 in a selected vertical position relative to the tube 86. A plurality of hooks 90 are coupled to an upper end of the IV pole 88 for supporting one or more IV bags (not shown) The base 84 includes a central hub 92 and five spokes 94 radiating substantially horizontally outwardly from the central hub 92. Casters 96 are coupled to distal ends of the spokes 94. If desired, IV pumps or other equipment may be hung on the hooks 90 or coupled to one or both of the poles 86, 88.

Figure 2:
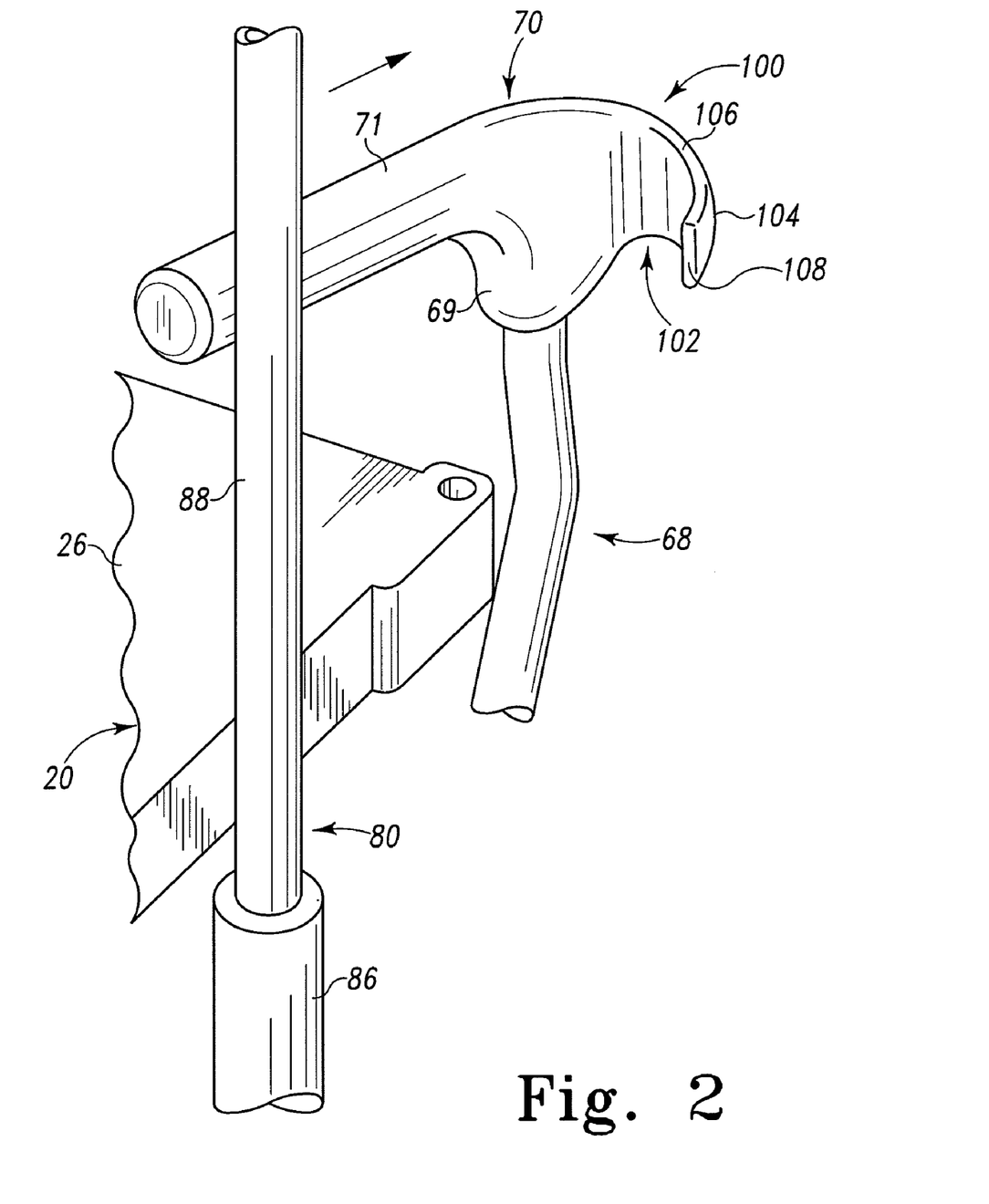
FIG. 2 is an enlarged perspective view of the right push handle and a portion of the IV pole showing the IV pole coupler comprising a hook that opens laterally inwardly toward the center of the stretcher and showing the IV pole spaced laterally inwardly of the IV pole coupler.
Figure 3:
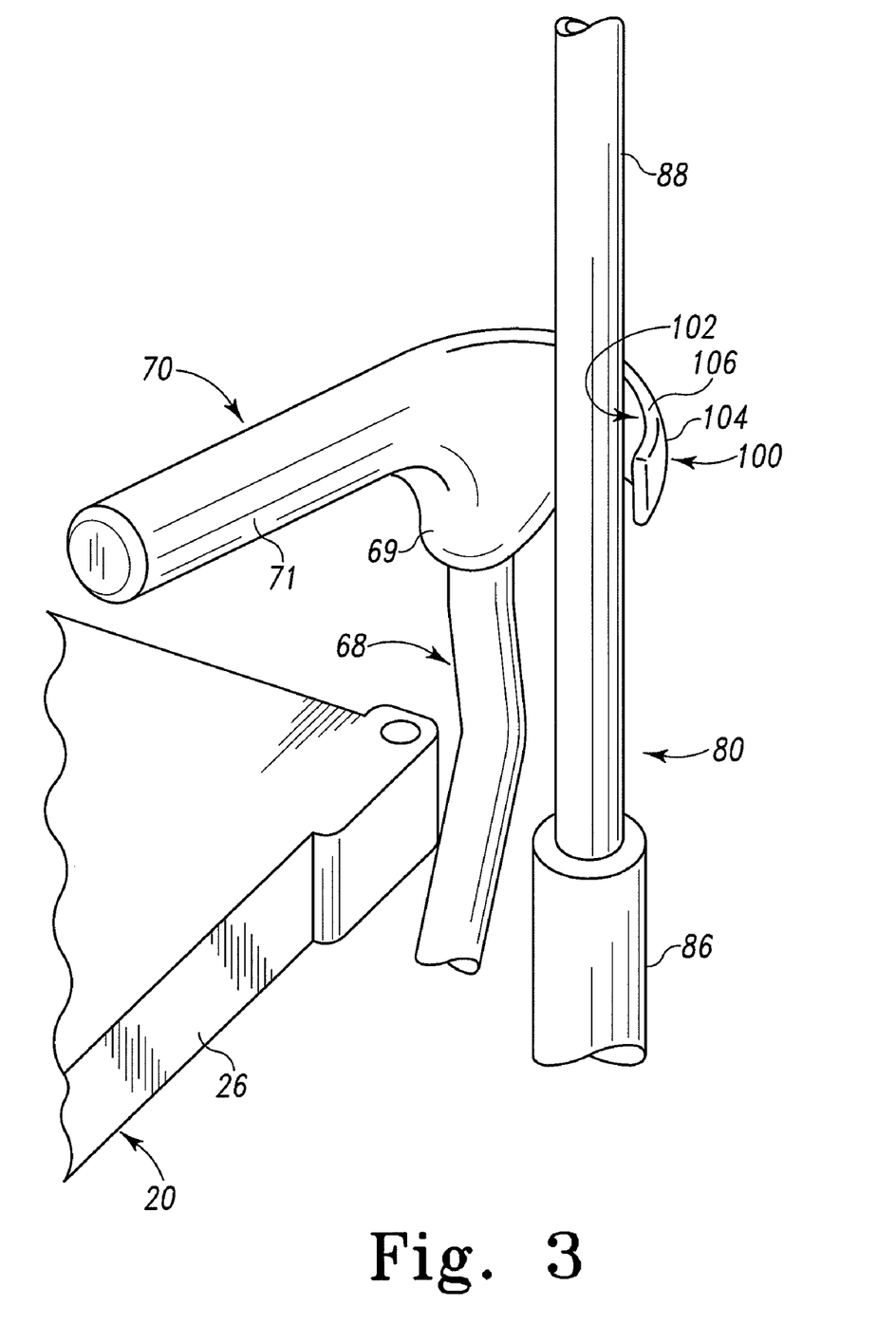
FIG. 3 is an enlarged perspective view, similar to FIG. 2, showing the IV pole moved into the IV pole coupler so that the IV pole coupler hooks around the IV pole.
Figure 4:
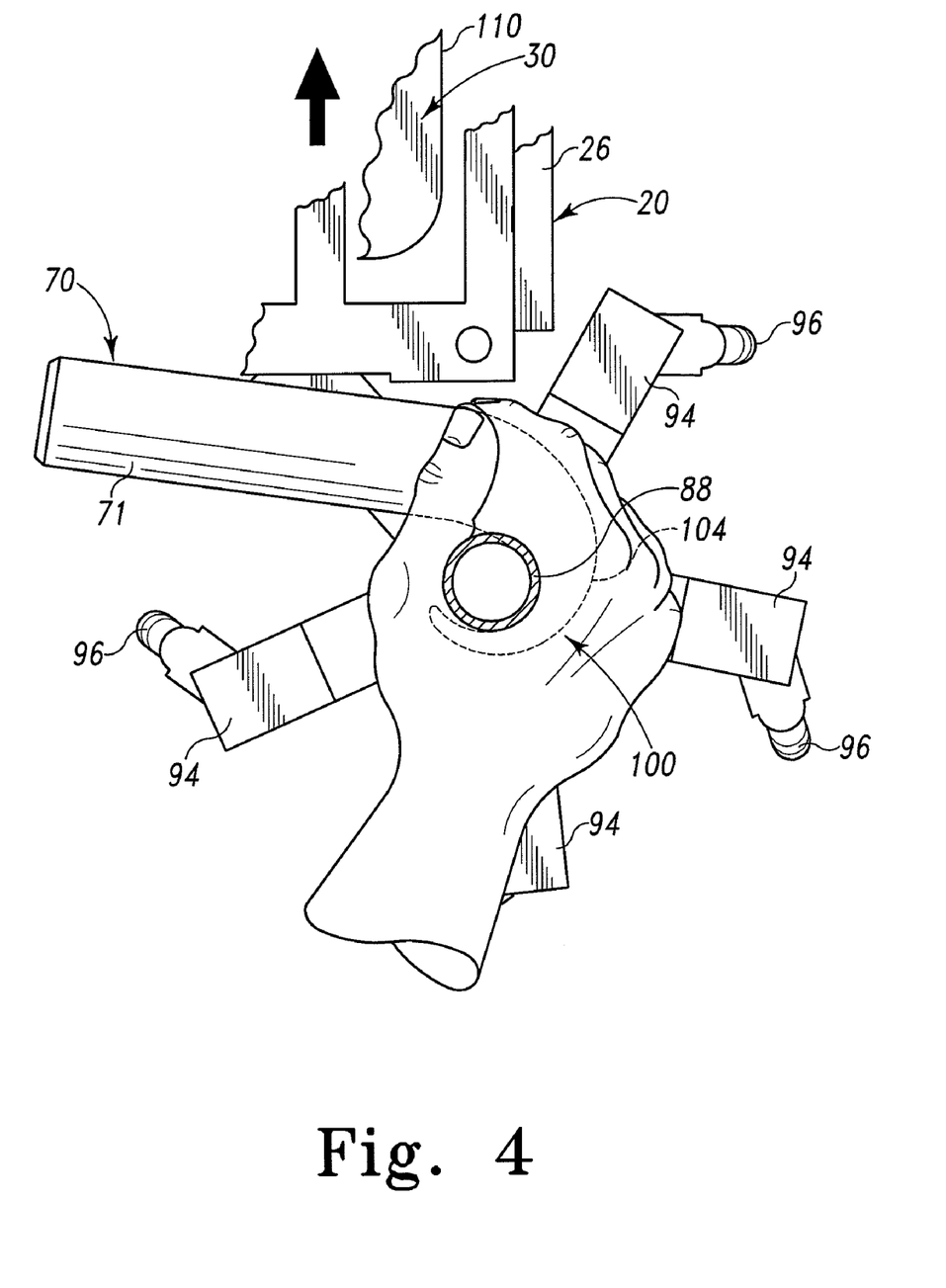
FIG. 4 is a top plan view showing a caregiver gripping or grasping with one hand the handle post of the push handle and the IV pole received in the IV pole coupler.

As shown in FIGS. 2-4, the handle post 70 of the push handle 68 has a generally upwardly extending first portion 69 and a second portion 71 that extends laterally inwardly relative to the first portion 69 when the push handle 68 is in the raised push position. An IV pole coupler 100 extends laterally outwardly relative to the upwardly extending first portion 69 of the handle post 70. As shown, for example, in FIGS. 2 and 3, the IV pole coupler 100 has a generally vertically-extending groove 102 configured to receive the IV pole 88. Illustratively, the vertically-extending groove 102 opens laterally inwardly toward a vertical plane passing through the longitudinal axis 40 of the frame 26. As shown in FIG. 4, the IV pole coupler 100 has a hook or flange portion 104 that is configured to hook around the IV pole 88 when the IV pole 88 is received in the vertically-extending groove 102. As shown in FIGS. 2 and 3, a top wall 106 of the flange portion 104 tapers downwardly toward a free end 108 thereof. As shown in FIG. 4, a portion of the IV coupler 100 extends outwardly past a side edge 110 of the deck 30. In the illustrated embodiment, the IV pole coupler 100 is integrally formed with the handle post 70 of the push handle 68. The IV pole coupler 100 and the handle post 70 of the push handle 68 are molded from a suitable plastic material, such as polypropylene or santoprene material. The extension post 72 and the pivot post 74 of the push handle 68 are in the form of extruded tubes having a circular cross section, and are made from rigid high strength, light weight materials, such as steel or aluminum.

In use, the IV pole 88 is movable from a position aligned with coupler 100 but spaced laterally inwardly therefrom, as shown in FIG. 2, to a position in which IV pole 88 is received in the vertically-extending groove 102 of coupler 100, as shown in FIG. 3. When IV pole 88 is received in groove 102 of coupler 100, a caregiver is able to simultaneously grasps the handle post 70 of the push handle 68 and the IV pole 88 with one hand, as shown in FIG. 4, and grasps the handle post 70 of the push handle 66 with the other hand and pushes the stretcher 20 along the floor 50 with the mobile IV stand 80 in tow. The simultaneous grasping of the handle post 70 and the pole 88, possibly along with the coupler 100, by the caregiver's hand retains the pole 88 in the IV pole coupler 100. If desired, the caregiver may grasp the handle post 70 at a position close to the IV pole 88 such that the outside edge of the caregiver's hand prevents the IV pole 88 from moving out of the groove 102 during transport. Thus, IV pole coupler 100 is integral with push handle 68 and provides an easy and convenient device for allowing a floor supported, wheeled IV pole stand to be transported simultaneously with stretcher 20. Additionally or alternatively, an IV pole coupler 100 may be provided on handle post 70 of push handle 66 as well.

Figure 5:
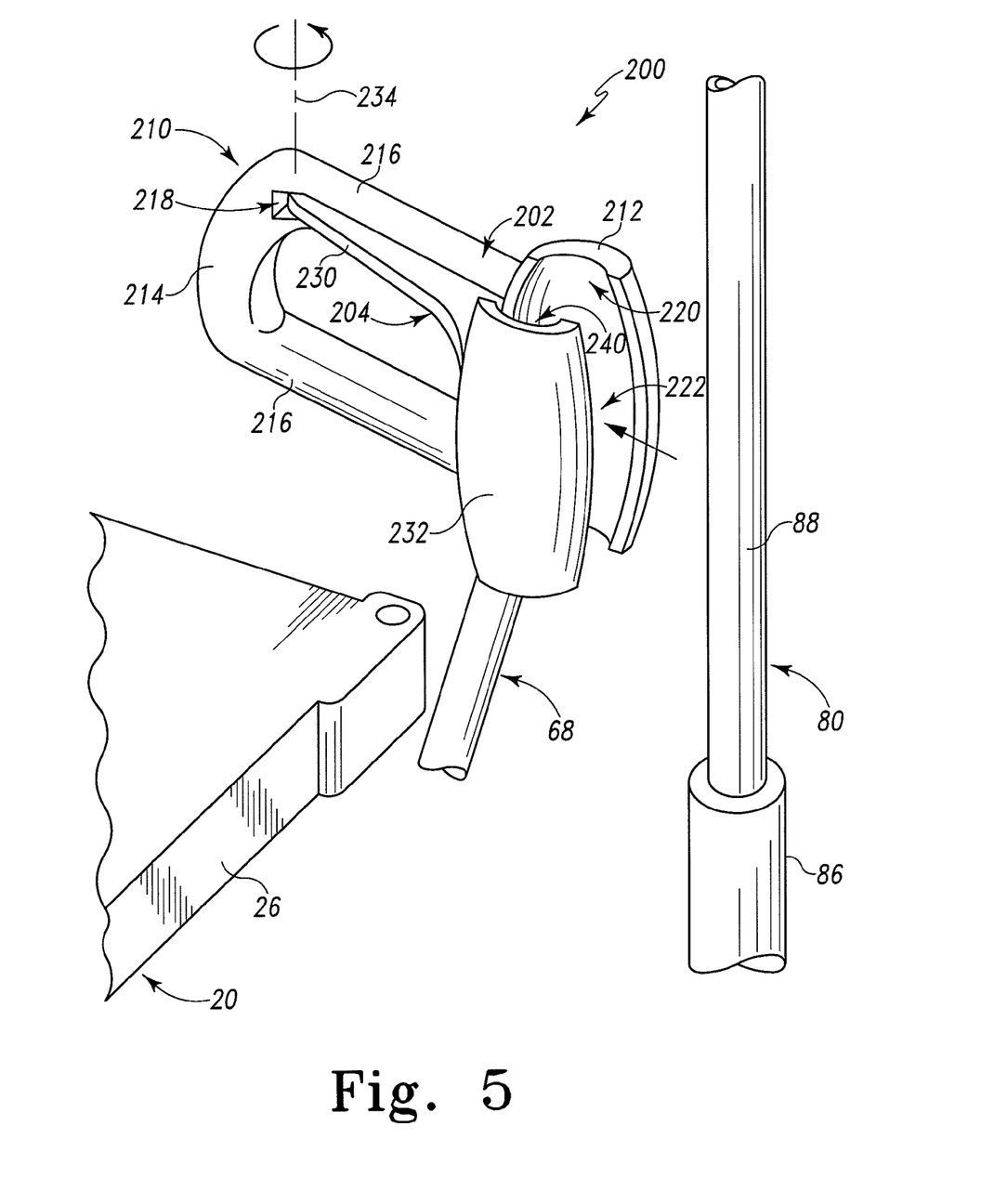
FIG. 5 is a perspective view of a second embodiment of the IV pole coupler having a handle and a lever arm that is movable relative to the handle between an open position and a closed position, the lever arm being shown in the open position in FIG. 5, showing the handle and the lever arm having complementary generally vertically-extending grooves and a mobile IV stand approaching an IV pole-receiving cavity defined by the complementary generally vertically-extending grooves.
Figure 6:
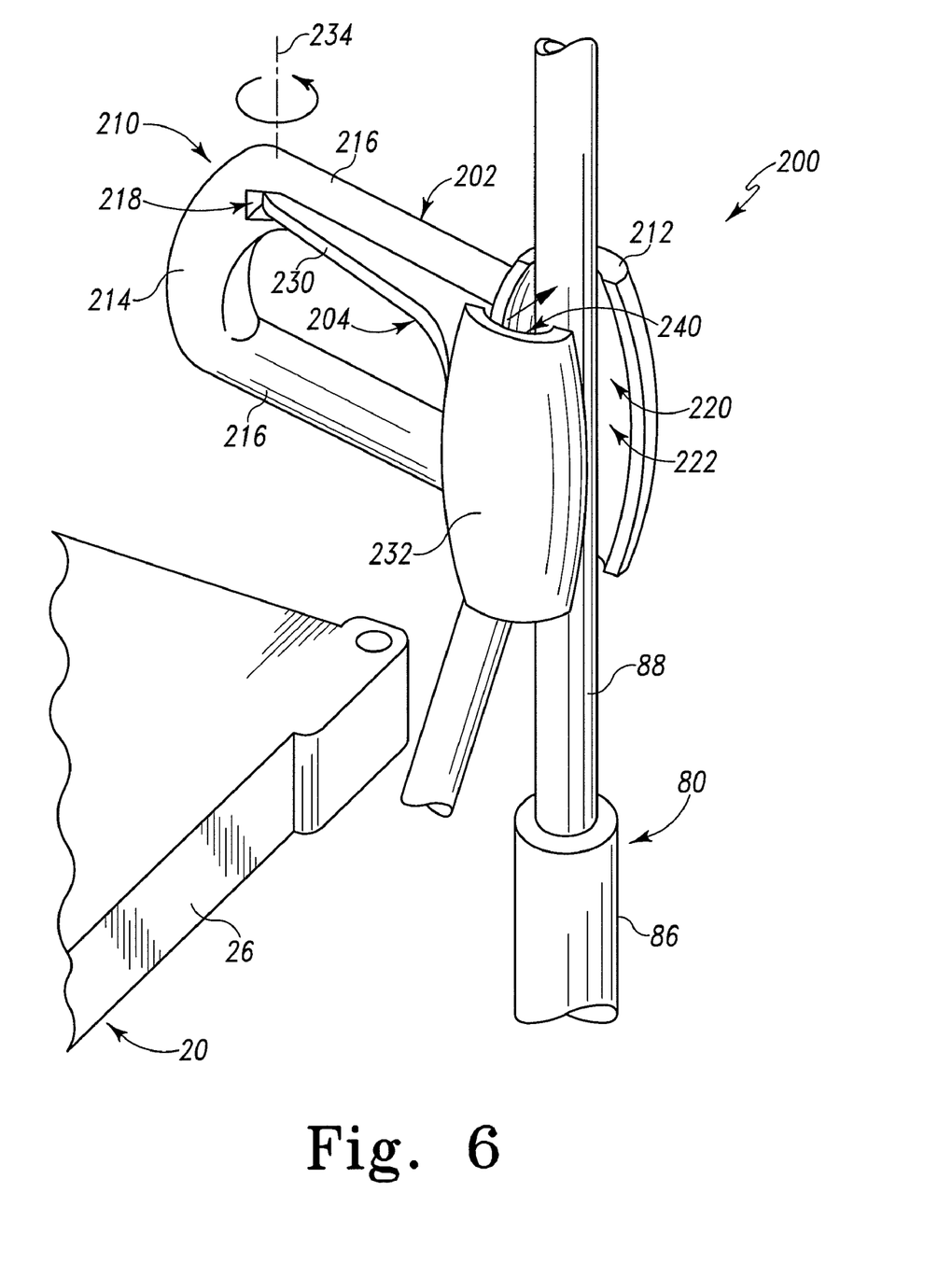
FIG. 6 is a perspective view similar to FIG. 5 showing the IV pole of the mobile IV stand positioned in the IV pole-receiving cavity.
Figure 7:
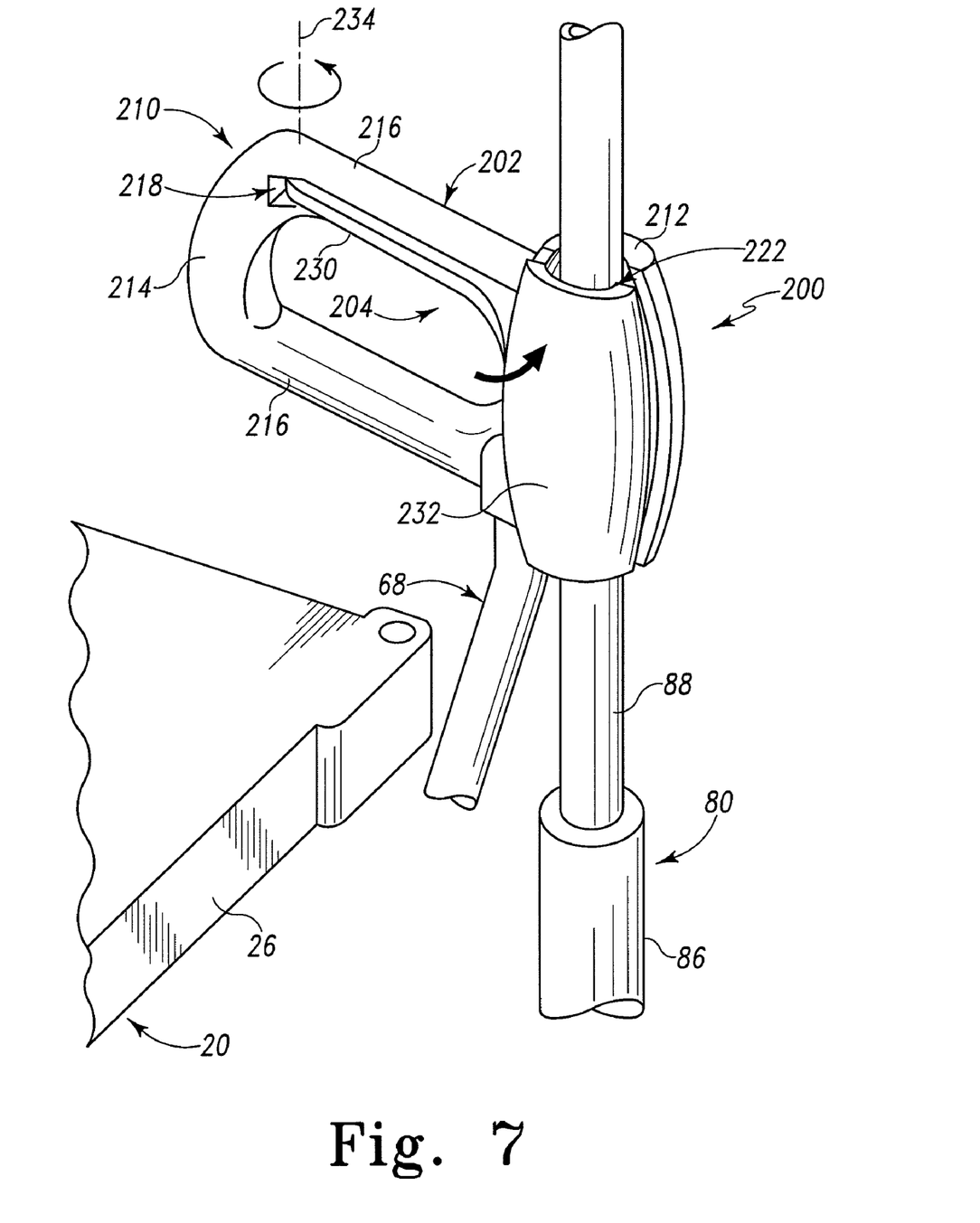
FIG. 7 is a perspective view similar to FIG. 6 showing the lever arm moved to its closed position to capture the IV pole within the IV pole-receiving cavity.

FIGS. 5-7 show a second embodiment 200 of the IV pole coupler 100. As shown in FIGS. 5-7, the IV pole coupler 200 comprises a handle 202 and a lever arm 204 that is movable relative to the handle 202 between an open position shown in FIGS. 5-6 and a closed position shown in FIG. 7. The handle 202 comprises a U-shaped body 210 and a vertically-extending flange 212. The lever arm 204 comprises a horizontally-extending arm 230 and a vertically-extending flange 232. The vertically-extending flanges 212, 232 of the handle 202 and the lever arm 204 have complementary generally vertically-extending grooves 220, 240 defining an IV pole-receiving cavity 222. The U-shaped body 210 has a vertically-extending bight 214 disposed between two horizontally-extending arms 216.

The horizontally-extending upper arm 216 of the handle 202 has an outwardly-opening recess 218 that extends along its longitudinal dimension. The lever arm 204 is mounted in the horizontally-extending recess 218 in the handle 202 for pivoting movement about a vertical axis 234 between the open position shown in FIGS. 5-6 allowing the IV pole to be situated in the IV pole-receiving cavity 222 and the closed position shown in FIG. 7 capturing the IV pole 88 in the IV pole-receiving cavity 222. In the illustrated embodiment, the handle 202 and the lever arm 204 are made from plastic, although other suitable materials, such as aluminum, may be used. Walls forming the grooves 220, 240 generally define an inner profile that generally corresponds to an outer profile of the IV pole 88.

Figure 8:
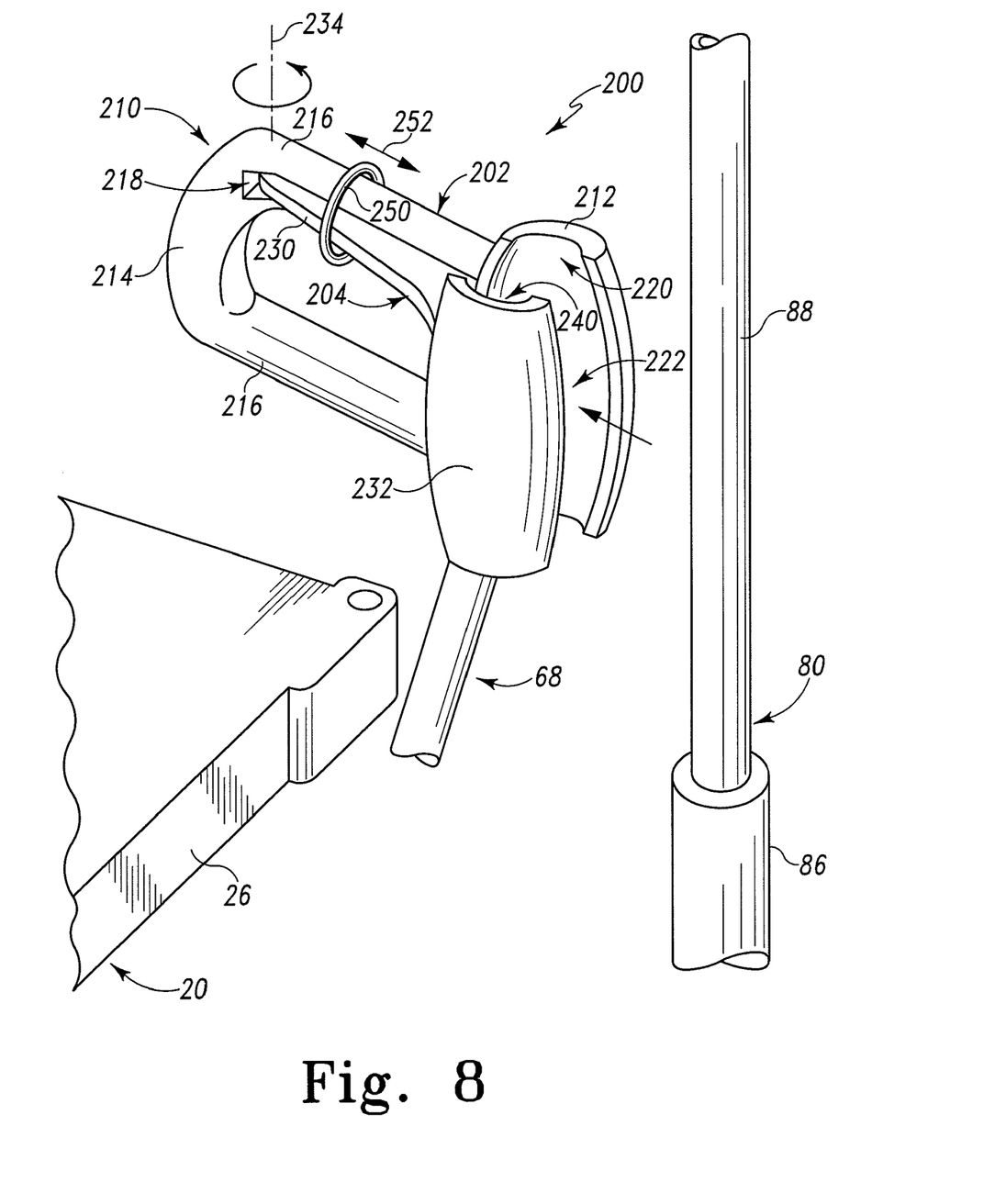
FIG. 8 is a perspective view of a third embodiment of the IV pole coupler similar to the IV pole coupler of FIG. 5, except that a sliding ring is mounted on the handle to hold the lever arm in its closed position.

FIG. 8 is a perspective view of a third embodiment of the IV pole coupler 100 similar to the IV pole coupler 200 of FIGS. 5-7, except that a sliding ring 250 is mounted on the horizontally-extending upper arm 216 of the handle 202 for movement along its longitudinal dimension as shown by a double-headed arrow 252. The sliding ring 250 is movable between a first position near the pivot axis 234 allowing the lever arm 204 to move between its open position (FIGS. 5-6) and its closed position (FIG. 7) and a second position near the IV pole-receiving cavity 222 to securely hold the lever arm 204 in its closed position to capture the IV pole 88 in the IV pole-receiving cavity 222. In some embodiments, a ratchet-type locking mechanism (not shown) is used for holding the lever arm 204 in its closed position. In still other embodiments, a rubber strap is used for holding the lever arm 204 in its closed position.

Figure 9:
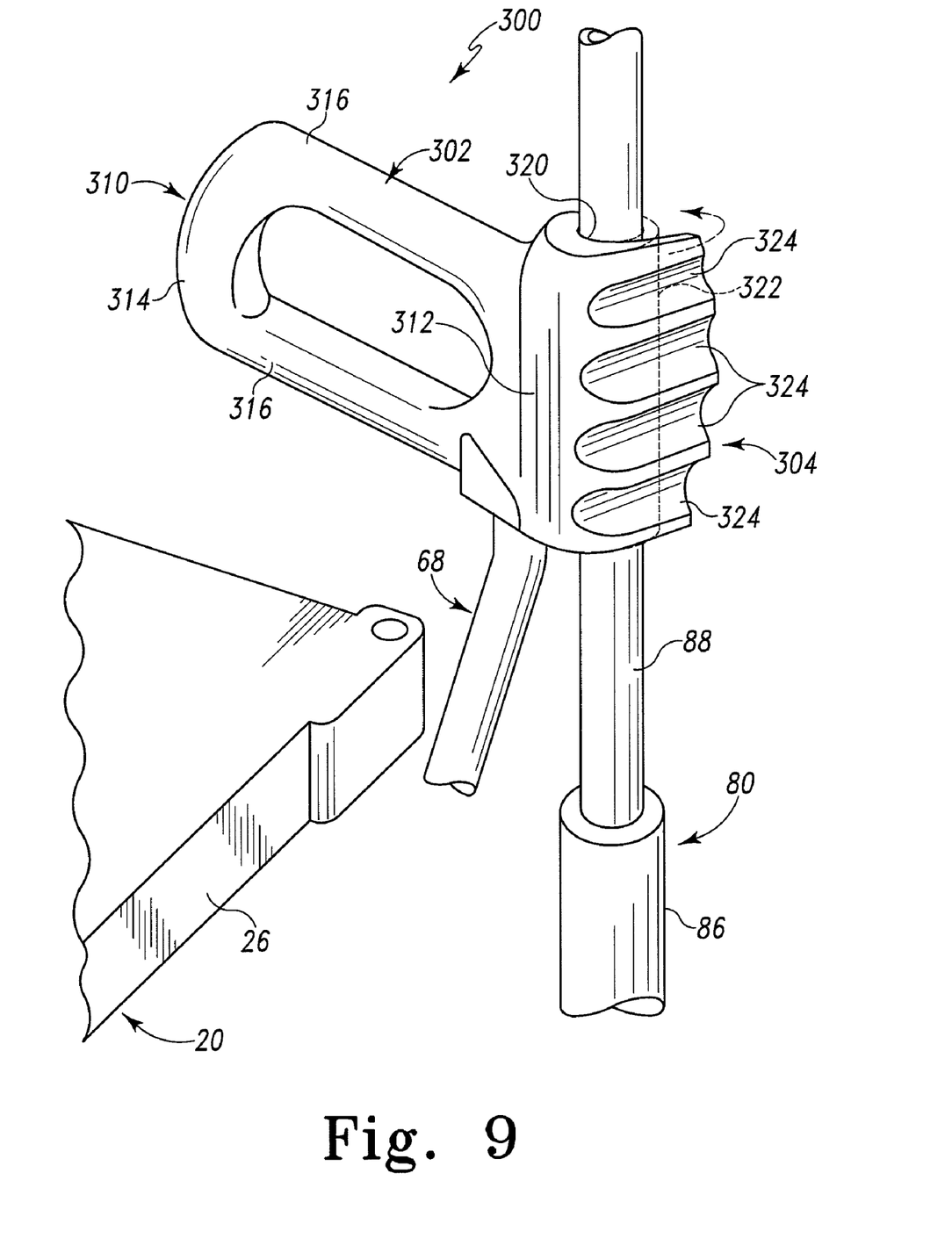
FIG. 9 is a perspective view of a fourth embodiment of the IV pole coupler having a handle defining a generally vertically-extending laterally outwardly-facing groove for receiving an IV pole and a flap of flexible material that extends outwardly from an outside edge of the groove that can be wrapped around the IV pole.

FIG. 9 is a perspective view of a fourth embodiment 300 of the IV pole coupler 100. The IV pole coupler 300 comprises a handle 302 and a flexible flap 304. The handle 302 comprises a U-shaped body 310 and a vertically-extending flange 312. The U-shaped body 310 has a vertically-extending bight 314 disposed between two horizontally-extending arms 316. The flange 312 has a generally vertically-extending groove 320 for receiving an IV pole 88. Illustratively, the vertically-extending groove 320 opens laterally outwardly relative to a vertical plane passing through the longitudinal axis 40 of the frame 26. The flexible flap 304 extends outwardly from an outside edge 322 of the groove 320. The hand of a caregiver or a transporter encircles the handle 302 and securely holds the flexible flap 304 around the IV pole 88 when the IV pole 88 situated in the groove 320 to stabilize it. The outer surface of the flap 304 has a plurality of grooves 324 to avoid inadvertent slippage of the caregiver's hand. In the illustrated embodiment, the handle 302 is made from plastic or aluminum and the flexible flap 304 is made from rubber, although other suitable materials may be used. In some embodiments, a malleable material, such as one or more wires or a thin band of metal material, may be included in the flap 304 to retain the flap 304 in its unwrapped condition as well as in its wrapped condition around the pole 88. In such embodiments, therefore, a slight amount of force is needed to wrap and unwrap the flap 304 relative to the pole 88 which is in contrast to the embodiment having only a flexible rubber flap which has a tendency to spring open when not being held by a caregiver around the pole 88. Any suitable device or method may be used for securing the flexible flap 304 to the flange 312, such as buttons, zipper, adhesives, heat sealing, sonic welding, sewing, etc.

Figure 10:
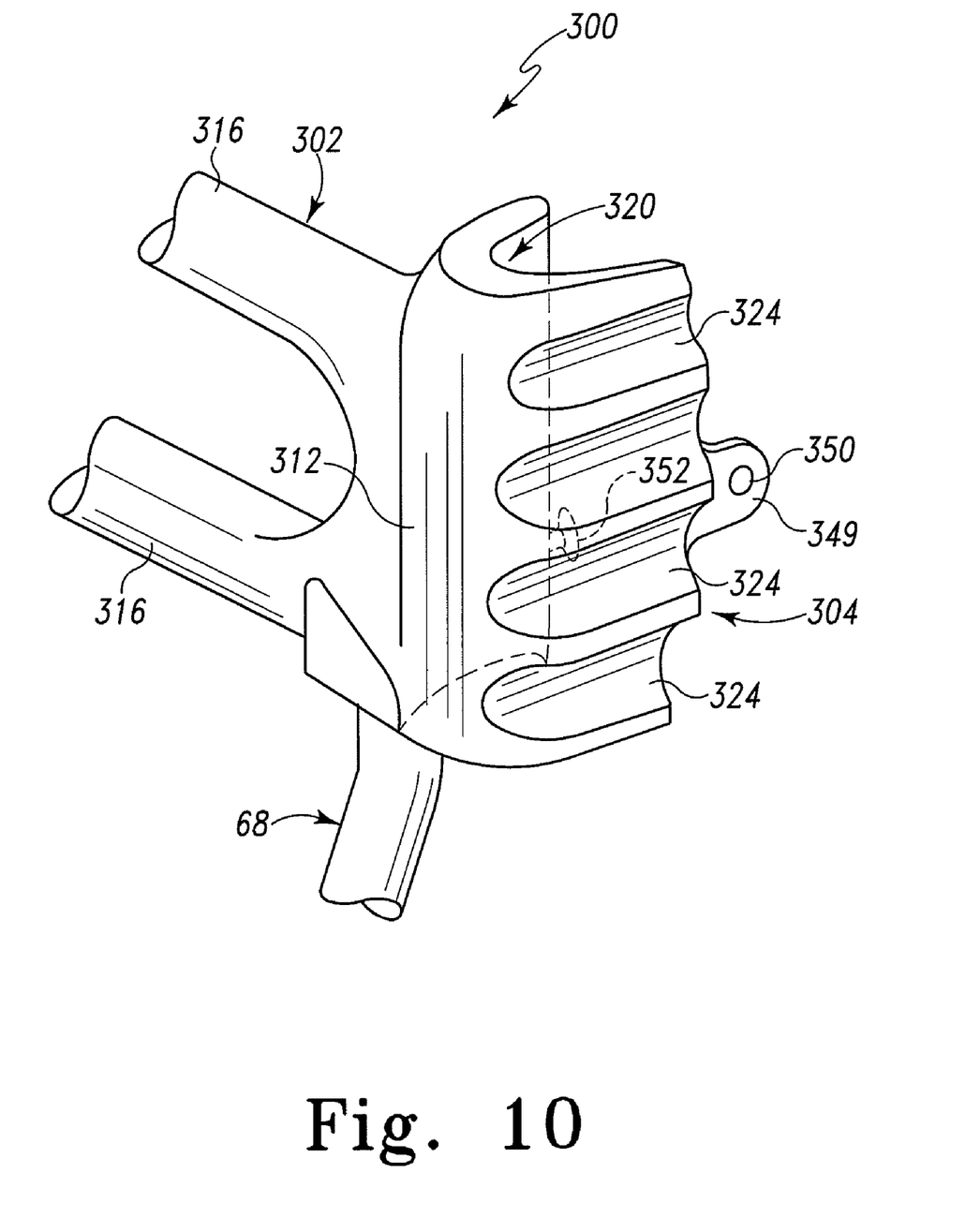
FIG. 10 is a perspective view of a fifth embodiment of the IV pole coupler similar to the IV pole coupler of FIG. 9, except that the flexible flap has a hole near its free end that can be fastened to a button on the handle on the opposite side of the vertically-extending groove.

FIG. 10 is a perspective view of a fifth embodiment of the IV pole coupler similar to the IV pole coupler of FIG. 9, except that the flexible flap 304 has a tab 349 with a hole 350 near its free end that couples or fastens to a button or a headed pin 352 located on the handle 302 on the opposite side of the groove 320 so as to hold the IV pole 88 in place in the groove 320 without the hand of the caregiver present. In some embodiments, the flexible tab 349 or the flap 304 has two or more holes (not shown) at different distances from its free end that are fastened or coupled to a button or a headed pin 332 on the handle 302 on the opposite side of the groove 320 to accommodate different sized IV poles.

Although certain illustrative embodiments have been described in detail above, variations and modifications exist within the scope and spirit of this disclosure as described and as defined in the following claims.

The invention claimed is:

1. A patient support apparatus for use with an IV pole supported on wheels, the apparatus comprising
   a patient support frame,
   a plurality of casters coupled to the frame and supporting the frame above a floor,
   a push handle coupled to the frame, and
   an IV pole coupler coupled to the push handle, wherein the push handle and IV pole coupler constructed as one piece having a generally J shape and are configured to be grasped by a user's hand simultaneously when the IV pole of the IV pole supported on wheels is received by the IV pole coupler to permit the IV pole supported on wheels to be transported in tandem with the patient support with the casters of the plurality of casters of the patient support apparatus and the wheels of the IV pole supported on wheels rolling along a floor simultaneously, wherein the IV pole coupler is devoid of any spring-loaded clamping elements and is devoid of any adjustment screws.

2. The apparatus of claim 1, wherein the IV pole coupler comprises a hook that hooks around the IV pole.

3. The apparatus of claim 1, wherein the push handle has a generally upwardly extending first portion, a handle post extending laterally inwardly relative to the first portion, and the IV pole coupler extends laterally outwardly relative to the first portion.

4. The apparatus of claim 3, further comprising a deck supported above the frame, wherein the IV pole coupler has a portion that extends outwardly past a side edge of the deck.

5. The apparatus of claim 3, wherein the IV pole coupler has a generally vertically-extending groove configured to receive the IV pole.

6. The apparatus of claim 5, wherein the generally vertically-extending groove opens laterally inwardly toward a vertical plane passing through a longitudinal centerline of the frame.

7. The apparatus of claim 5, wherein the IV pole coupler has a flange portion that is configured to wrap around the IV pole when the IV pole is received in the vertically-extending groove.

8. The apparatus of claim 7, wherein a top wall of the flange portion tapers downwardly toward a free end thereof.

9. The apparatus of claim 1, wherein the frame comprises a lower frame and an upper frame supported by the lower frame, the push handle is coupled to the upper frame, and the push handle is movable between a use position in which the IV pole coupler is located above the upper frame and a storage position in which the IV pole coupler is located below the upper frame.

10. The apparatus of claim 1, wherein the IV pole coupler has a first portion and a second portion that is movable relative to the first portion between a first position coupling the IV pole to the handle and a second position allowing the IV pole to be decoupled from the handle.

11. The apparatus of claim 10, wherein the first and second portions of the IV pole coupler engage first and second portions of the IV pole when the second portion is in the first position.

12. The apparatus of claim 10, wherein the first and second portions have complementary generally vertically-extending grooves such that the grooves are located on the opposite sides of the IV pole when the IV pole is received in a cavity defined by the grooves and the second portion is in the first position.

13. The apparatus of claim 12, wherein walls forming the grooves define an inner profile that generally corresponds to an outer profile of the IV pole.

14. The apparatus of claim 10, comprising a latch movable between a latched position in which the second portion is held in the first position and an unlatched position in which the second portion is movable between the first and second positions.

15. The apparatus of claim 10, further comprising a ring that is movable along the first portion between a locked position in which the second portion is held in the first position and an unlocked position in which the second portion is movable between the first and second positions.

16. The apparatus of claim 1, wherein the IV pole coupler comprises a flexible flap that is configured to deformingly wrap around the IV pole.

17. The apparatus of claim 16, further comprising a flap coupler to retain the flexible flap in a wrapped condition around the IV pole.

18. The apparatus of claim 17, wherein the flap coupler comprises a headed pin secured to the push handle and a hole in the flexible flap that receives the headed pin.

19. A patient support apparatus for use with an IV pole supported on wheels, the apparatus comprising a patient support frame, a plurality of casters coupled to the frame and supporting the frame above a floor, and a push handle coupled to the frame and having integrated as one piece therewith an IV pole coupler, the push handle and the IV pole together forming a general J shape with a generally vertically-extending groove for receiving the IV pole so that a caregiver can grip the push handle and the IV pole with one hand as the caregiver maneuvers the patient support apparatus and the IV pole along the floor such that the IV pole supported on wheels is transported in tandem with the patient support with the casters of the plurality of casters of the patient support apparatus and the wheels of the IV pole supported on wheels rolling along a floor simultaneously, wherein the IV pole coupler is devoid of any spring-loaded clamping elements and is devoid of any adjustment screws.

20. The apparatus of claim 19, wherein the push handle comprises first and second push handles, and the IV pole coupler with the vertically-extending groove for receiving the IV pole is arranged in the first push handle so that a caregiver can grip the first push handle and the IV pole with one hand and grip the second push handle with the other hand as the caregiver maneuvers the patient support apparatus and the IV pole along the floor.

21. The apparatus of claim 19, wherein the push handle has a proximal end coupled to the frame and a distal end defining a handle post, and the IV pole coupler with the generally vertically-extending groove is arranged in the handle post.

22. The apparatus of claim 21, comprising a deck supported above the frame, wherein the handle post has a portion that extends outwardly past a side edge of the deck, and the generally vertically-extending groove is arranged in the outwardly extending portion of the handle post.

23. The apparatus of claim 21, wherein the handle post has a generally vertically-extending portion and a generally horizontally extending portion that extends generally perpendicularly to a longitudinal axis of the patient support apparatus, and the IV pole coupler with the generally vertically-extending groove is arranged in the generally vertically-extending portion of the handle post.

24. The apparatus of claim 23, wherein the generally vertically-extending portion of the handle post has a flange portion that is configured to wrap around the IV pole when the IV pole is received in the vertically-extending groove.

25. The apparatus of claim 19, wherein the frame comprises a lower frame and an upper frame supported above the lower frame, the push handle has a proximal end coupled to the upper frame and a distal end defining a handle post, and the push handle is movable between a use position in which the handle post is located above the upper frame and a storage position in which the handle post is located below the upper frame.

26. The apparatus of claim 19, wherein the push handle is located on a right hand side of the patient support apparatus.

27. The apparatus of claim 19, wherein the generally vertically-extending groove faces a caregiver as the caregiver maneuvers the patient support apparatus and the IV pole along the floor.

* * * * *